United States Patent [19]

Shinohara et al.

[11] Patent Number: 5,245,066
[45] Date of Patent: Sep. 14, 1993

[54] METHOD FOR PREPARING HEXAMETHYLCYCLOTRISILAZANE

[75] Inventors: Toshio Shinohara, Takasaki; Akio Yokoo, Annaka; Muneo Kudo, Annaka; Kazuyuki Matsumura, Annaka, all of Japan

[73] Assignee: Shin-Etsu Chemical Co., Ltd., Tokyo, Japan

[21] Appl. No.: 933,202

[22] Filed: Aug. 21, 1992

[30] Foreign Application Priority Data

Aug. 22, 1991 [JP] Japan .................................. 3-237270

[51] Int. Cl.$^5$ ............................................... C07F 7/10
[52] U.S. Cl. .................................................... 556/409
[58] Field of Search ......................................... 556/409

[56] References Cited

U.S. PATENT DOCUMENTS

| | | | |
|---|---|---|---|
| 2,579,416 | 12/1951 | Cheronis | 556/409 X |
| 3,481,964 | 12/1969 | Ismail et al. | 556/409 X |
| 4,577,039 | 3/1986 | Arkles et al. | 556/409 |
| 4,855,469 | 8/1989 | Baile et al. | 556/409 |
| 5,075,474 | 12/1990 | Ohsaki et al. | 556/409 |

*Primary Examiner*—Paul F. Shaver
*Attorney, Agent, or Firm*—Birch, Stewart, Kolasch & Birch

[57] ABSTRACT

Hexamethylcyclotrisilazane is prepared by reacting dimethyldichlorosilane with ammonia at a temperature between −20° C. and 20° C. Preferably, ammonia is blown into dimethyldichlorosilane at the temperature, and the reaction mixture is washed with 20% or higher alkaline water within one hour from the end of reaction for removing ammonium chloride by dissolving it in the water. Then hexamethylcyclotrisilazane of high purity is prepared in high yields. The method can be scaled up for commercial manufacture.

7 Claims, 1 Drawing Sheet

BEST AVAILABLE COPY
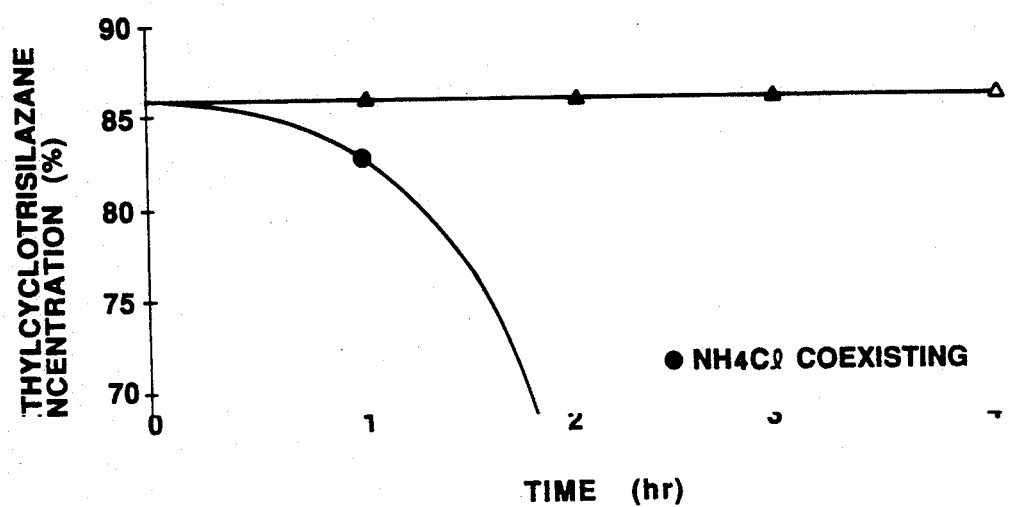

METHOD FOR PREPARING HEXAMETHYLCYCLOTRISILAZANE

TECHNICAL FIELD

This invention relates to a method for preparing hexamethylcyclotrisilazane suitable for use as electronics material or the like.

BACKGROUND OF THE INVENTION

For the preparation of hexamethylcyclotrisilazane, it is known to react dimethyldichlorosilane with ammonia according to the following reaction scheme (see J. Am. Chem. Soc., 70, 3888-91, 1948).

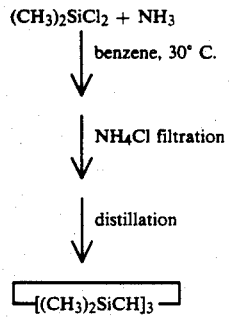

This method involves reacting dimethyldichlorosilane with ammonia in benzene at 30° C., removing ammonia chloride by-product by filtration through a glass filter or the like, and distilling the reaction product to isolate hexamethylcyclotrisilazane.

Undesirably, this method can produce hexamethylcyclotrisilazane in a very low yield of about 36%. In addition, it is difficult to effectively remove the ammonium chloride by-product by filtration and even the subsequent distillation cannot remove it satisfactorily. The thus obtained product contains a relatively large amount of chloride and other impurities. That is, the final product has low purity. For this purity problem, the hexamethylcyclotrisilazane obtained by the conventional method is not regarded suitable as photoresist processing agents and other electronics materials which currently continue a remarkable advance.

SUMMARY OF THE INVENTION

Therefore, an object of the present invention is to provide a novel and improved commercial scale method for preparing hexamethylcyclotrisilazane of quality in high yields.

The inventors have found that by reacting dimethyldichlorosilane with ammonia at a temperature between −20° C. and 20° C., preferably by blowing ammonia into dimethyldichlorosilane, and then washing the reaction mixture with alkaline water having an alkali concentration of at least 20% within one hour from the end of reaction for dissolving and removing the ammonium chloride resulting from the reaction, hexamethylcyclotrisilazane of high purity can be obtained in high yields. This method is compatible with commercial scale production.

More particularly, the inventors have found that when the temperature for reaction between dimethyldichlorosilane and ammonia is reduced to a level lower than those employed in the conventional method, that is, to a temperature between −20° C. and 20° C., quite unexpectedly, the reaction can effectively take place so that the yield of the end product, hexamethylcyclotrisilazane may remarkably jump up.

At the end of reaction between dimethyldichlorosilane and ammonia, the reaction system was allowed to stand in the co-presence of ammonium chloride for investigating how the hexamethylcyclotrisilazane varied with time. A drastic change with time was found as shown in FIG. 1. The concentration of hexamethylcyclotrisilazane slowly lowered in an initial period of up to 1 hour after the end of reaction, and then drastically lowered, reaching to about 60% after 2 hours. Surprisingly, if the ammonium chloride was removed within one hour from the end of reaction, the concentration of hexamethylcyclotrisilazane then remained substantially unchanged for many hours.

It is thus presumed that ammonium chloride has some catalysis on the reaction product, causing hexamethylcyclotrisilazane to polymerize so that the concentration thereof lowers with the lapse of time, and that the filtration step allowing hexamethylcyclotrisilazane and ammonium chloride to coexist for a long time is a main cause for the low purity and yield problem associated with the conventional method.

Based on these results, the inventors have found that by blowing ammonia into dimethyldichlorosilane for reaction therebetween at a temperature of from −20° C. to 20° C. and then washing the reaction mixture with alkaline water having an alkali concentration of at least 20% within one hour from the end of reaction, the ammonium chloride resulting from the reaction can be readily and quickly dissolved and removed and therefore, hexamethylcyclotrisilazane of high purity can be obtained in high yields.

BRIEF DESCRIPTION OF THE DRAWING

The only FIGURE, FIG. 1 is a graph showing a change with time of the concentration of hexamethylcyclotrisilazane in a reaction mixture obtained by reacting dimethyldichlorosilane with ammonia.

DETAILED DESCRIPTION OF THE INVENTION

According to the present invention, hexamethylcyclotrisilazane is prepared by reacting dimethyldichlorosilane with ammonia at a temperature of from −20° C. to 20° C.

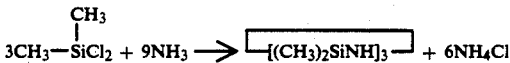

Preferably, dimethyldichlorosilane and ammonia are used such that about 3 to 4 mol, especially about 3 to 3.5 mol of ammonia is available per mol of dimethyldichlorosilane. Reaction is effected at a temperature of from −20° C. to 20° C. No effective reaction takes place below −20° C. whereas more octamethylcyclotetrasilazane, one of by-products, is formed above 20° C.

The reaction may be carried out in an organic solvent which is inert to the reaction system. Examples of the organic solvent include hydrocarbon solvents such as benzene, n-hexane, cyclohexane, and toluene, ethers such as tetrahydrofuran and dioxane, and any other solvents which are stable in the reaction system.

In the practice of the present invention, after ammonia has been blown into dimethyldichlorosilane to effect reaction therebetween at the specified temperature to predominantly form hexamethylcyclotrisilazane and ammonium chloride, the reaction mixture is desirably washed with alkaline water for readily and quickly removing the ammonium chloride by dissolving it in the water.

Washing with alkaline water should preferably be conducted within one hour, especially within 30 minutes from the end of ammonia blowing. Washing after more than one hour would result in hexamethylcyclotrisilazane of lower purity. The alkaline water is water containing an alkali metal hydroxide such as sodium hydroxide, potassium hydroxide and lithium hydroxide in a concentration of 20% by weight or higher. Washing alkaline water having a concentration of less than 20% would subject the hexamethylcyclotrisilazane to hydrolysis, resulting in a low yield thereof.

After the ammonium chloride is dissolved, the aqueous and organic layers are separated. The organic layer is subject to vacuum distillation, obtaining the end product, hexamethylcyclotrisilazane.

The method of the present invention has the advantage that hexamethylcyclotrisilazane can be produced in high yields. When ammonium chloride is removed within one hour from the end of reaction, there is obtained a high purity hexamethylcyclotrisilazane product which contains a minimized amount of chlorides and other impurities. The hexamethylcyclotrisilazane product by the present invention is thus well suitable for use as photoresist agents and other electronics materials.

EXAMPLE

Examples of the present invention are given below by way of illustration and not by way of limitation.

EXAMPLE 1

A 3-liter, four-necked flask equipped with a stirrer, dry ice/acetone condenser, thermometer, and gas inlet tube was charged with 387 grams (3 mol) of dimethyldichlorosilane and 900 grams of toluene. Into the solution at 20° C., 155.4 grams (9.1 mol) of ammonia was blown over 2 hours for effecting reaction. The contents were poured into a 10-liter separatory flask equipped with a stirrer, into which 1350 grams of water containing 20% by weight of sodium hydroxide. The mixture was stirred for ½ hour for dissolving ammonium chloride in the aqueous layer and thereafter, separated into the aqueous and organic layers. The organic layer was subjected to vacuum distillation, obtaining 158 grams of hexamethylcyclotrisilazane as a fraction having a boiling point of 85° C. at a pressure of 30 mmHg (yield 72%).

EXAMPLE 2

The procedure of Example 1 was repeated except that the reaction temperature was −20° C., obtaining 175.6 grams of hexamethylcyclotrisilazane (yield 80%).

COMPARATIVE EXAMPLE 1

A 500-ml, four-necked flask equipped with a stirrer, dry ice/acetone condenser, thermometer, and gas inlet tube was charged with 64.5 grams (0.5 mol) of dimethyldichlorosilane and 150 grams of toluene. Into the solution at 30° C., 52 grams (3.06 mol) of ammonia was blown over 2 hours for effecting reaction. At the end of reaction, the reaction solution was passed through a glass filter to remove ammonium chloride resulting from the reaction. The filtrate was subjected to vacuum distillation, obtaining 15.4 grams of hexamethylcyclotrisilazane (yield 42%).

EXAMPLES 3-4 AND COMPARATIVE EXAMPLES 2-3

A 500-ml, four-necked flask equipped with a stirrer, dry ice/acetone condenser, thermometer, and gas inlet tube was charged with 64.5 grams (0.5 mol) of dimethyldichlorosilane and 150 grams of toluene. Into the solution at the temperature shown in Table 1, 52 grams (3.06 mol) of ammonia was blown over 2 hours for effecting reaction. The contents were poured into a 2-liter separatory flask equipped with a stirrer, into which 225 grams of water containing 20% by weight of sodium hydroxide. The mixture was stirred for ¼ hour for dissolving ammonium chloride in the aqueous layer and thereafter, separated into the aqueous layer containing ammonium chloride and the organic layer containing a silazane product. The organic layer was subjected to vacuum distillation, obtaining hexamethylcyclotrisilazane in the amount and yield shown in Table 1.

TABLE 1

|  | Reaction temperature (°C.) | Hexamethylcyclotrisilazane Amount* (g) | Yield (%) |
| --- | --- | --- | --- |
| Comparative Example 2 | −30 | 18.3 | 50 |
| Example 3 | −20 | 29.3 | 80 |
| Example 4 | 20 | 26.4 | 72 |
| Comparative Example 3 | 30 | 17.4 | 42 |

*theory 36.6 grams

As is evident from Table 1, reaction at temperatures between −20° C. and 20° C. (Examples 3 and 4) produces hexamethylcyclotrisilazane in higher yields than at temperatures outside the range (Comparative Examples 2 and 3).

We claim:
1. A method for preparing hexamethylcyclotrisilazane comprising the steps of:
    reacting dimethyldichlorosilane with ammonia at a temperature between −20° C. and 20° C. in an organic solvent which is inert to the reaction system and does not contain water, and
    washing the reaction mixture with alkaline water having an alkali concentration of at least 20% within one hour from the end of reaction for dissolving and removing the ammonium chloride resulting from the reaction.
2. The method for preparing hexamethylcyclotrisilazane according to claim 1, wherein the organic solvent is a hydrocarbon.
3. The method for preparing hexamethylcyclotrisilazane according to claim 1, wherein the organic solvent is an ether.
4. The method for preparing hexamethylcyclotrisilazane according to claim 1, wherein 3-4 mol of ammonia is used per mol dimethyldichlorosilane.
5. The method for preparing hexamethylcyclotrisilazane according to claim 2, wherein the organic solvent is selected from the group consisting of benzene, n-hexane, cyclohexane and toulene.
6. The method for preparing hexamethylcyclotrisilazane according to claim 3, wherein the organic solvent is selected from the group consisting of tetrahydrofuran and dioxane.
7. The method for preparing hexamethylcyclotrisilazane according to claim 1, wherein the alkaline water is water containing an alkali metal hydroxide selected from the group consisting of sodium hydroxide, potassium hydroxide and lithium hydroxide.

* * * * *